(12) United States Patent
Rao et al.

(10) Patent No.: US 6,834,117 B1
(45) Date of Patent: Dec. 21, 2004

(54) X-RAY DEFECT DETECTION IN INTEGRATED CIRCUIT METALLIZATION

(75) Inventors: Satyavolu Papa Rao, Dallas, TX (US); Basab Chatterjee, Plano, TX (US); Richard L. Guldi, Dallas, TX (US)

(73) Assignee: Texas Instruments Incorporated, Dallas, TX (US)

( * ) Notice: Subject to any disclaimer, the term of this patent is extended or adjusted under 35 U.S.C. 154(b) by 726 days.

(21) Appl. No.: 09/679,796

(22) Filed: Oct. 5, 2000

Related U.S. Application Data

(60) Provisional application No. 60/168,204, filed on Nov. 30, 1999.

(51) Int. Cl.[7] .................................................. G06K 9/00
(52) U.S. Cl. ........................ 382/149; 382/145; 438/16; 438/17; 250/370.01
(58) Field of Search ................................ 382/141, 145, 382/147, 149, 151; 438/16, 17; 378/51–69, 140, 145–161, 362.03; 250/370.01, 370.08, 370.09, 370.11, 363.02, 363.01, 363.62

(56) References Cited

U.S. PATENT DOCUMENTS

| | | | | |
|---|---|---|---|---|
| 3,723,873 A | * | 3/1973 | Witteles | 324/765 |
| 4,206,360 A | * | 6/1980 | LeMay | 378/12 |
| 4,266,135 A | * | 5/1981 | Kuwik et al. | 378/16 |
| 5,245,191 A | * | 9/1993 | Barber et al. | 250/363.04 |
| 5,802,137 A | * | 9/1998 | Wilkins | 378/85 |
| 5,966,424 A | * | 10/1999 | Liu | 378/98.8 |
| 6,031,892 A | * | 2/2000 | Karellas | 378/98.3 |
| 6,414,752 B1 | * | 7/2002 | Sullivan et al. | 356/237.5 |

* cited by examiner

*Primary Examiner*—Bhavesh M. Mehta
*Assistant Examiner*—Ali Bayat
(74) *Attorney, Agent, or Firm*—Jacqueline J. Garner; W. James Brady, III; Frederick J. Telecky, Jr.

(57) ABSTRACT

A system (25) for detecting defects in a semiconductor wafer (10), such defects including voids (V) present in metal conductors (2, 4) and plugs (7), is disclosed. An x-ray source (20) irradiates the wafer (10) through a first aperture array (24) having openings (26); a second aperture array (28) is located on the opposite side of the wafer (10) from the source (20), and has openings (30) that are aligned and registered with the openings (26) in the first aperture array (24). An array of x-ray detectors (31) is located adjacent to the second aperture array (28), with each detector (31) associated with one of the openings (30) of the second aperture array (28). The detectors (31) communicate signals regarding the magnitude of x-ray energy that is transmitted through wafer (10) at locations defined by the openings (26, 30) through aperture arrays (24, 28), to an analysis computer (34). A wafer translation system (32) indexes or otherwise moves the wafer (10) between the aperture arrays (24, 28). The analysis computer (34) generates an x-ray image of the wafer (10) from the detected x-ray energy, or alternatively compares the detected x-ray energy at locations of wafer (10) to automatically detect and distinguish defects.

19 Claims, 2 Drawing Sheets

X-RAY DEFECT DETECTION IN INTEGRATED CIRCUIT METALLIZATION

CROSS-REFERENCE TO RELATED APPLICATIONS

This application claims priority under 35 USC § 119(e)(1) of provisional application No. 60/168,204 filed Nov. 30, 1999.

STATEMENT REGARDING FEDERALLY SPONSORED RESEARCH OR DEVELOPMENT

Not applicable.

BACKGROUND OF THE INVENTION

This invention is in the field of integrated circuit manufacturing, and is more specifically directed to the non-destructive detection of defects in metal conductors of integrated circuits.

A critical step in the manufacture of integrated circuits is the formation of metal a conductors. Upper levels of conductors in integrated circuits are typically formed of copper or aluminum metallization, in order to bear the relatively high currents required in the distribution of power in the integrated circuit. As is known in the art, an upper current density limit for metal conductors is set to a level that avoids electromigration and other current-dependent voiding. This limit typically determines the minimum line width for the conductors in the integrated circuit, which is often a major factor upon which the overall integrated circuit chip area depends. In order to minimize the chip area required for realization of complex integrated circuits such as digital signal processors (DSPs) or microprocessors, multiple metallization levels are now quite common in the art, despite the complex manufacturing processing required for their fabrication.

Voiding in metal conductors is an important defect that can occur in the fabrication of thin, closely-spaced, metal conductors, particularly in multiple layers. Voids may be caused in the deposition of the metal film, as a result of metal etch, or by unintended corrosion during processing. Voids can also be caused by migration of atoms during thermal processing, or due to electrical stress; voids in metal conductors can also be present because of the inability of large grains to fill gaps, particularly in small geometries and over topography. Because of the yield loss due to defective metal lines, and also considering later-life reliability hazards resulting from the increased current density borne by a conductor in the locality of a void, the prevention of voids in metal conductors is of extreme importance in modern integrated circuit manufacturing.

In previous years, metal voids could be readily detected by visual inspection of the integrated circuits during or after their manufacture. Additionally, the reduction in metal conductors to the sub-micron range has not only reduced the optical visibility of the conductors, but has also increased the number of conductors that may be formed in a given chip area, eliminating the practicality of such visual inspection, even on a meaningful spot-check basis. This reduction in feature size has also reduced the minimum size of a killing void further below the visibility of optical microscopy. In addition, the presence of voids within the body of a conductor line cannot be detected by visual or scanning electron microscopy (SEM) techniques that are currently in use. Particularly in damascene copper structures, voids are typically buried in this manner, and are thus optically invisible, regardless of the conductor dimensions. The implementation of multiple metal levels has also limited visual inspection, because the opacity of the upper metal levels prevents top-side visual inspection of underlying metal conductors.

As a result, conventional inspection techniques now rely upon destructive techniques. Typically, sample wafers from the manufacturing line are cross-sectioned, and the cross-sections are examined by SEM for a measure of the metal film quality. The destructive nature of this inspection of course minimizes the number of samples that may be inspected by SEM. Furthermore, the nature of SEM precludes the viewing of more than a small number of locations of the wafer within each sample. The preparation of the cross-sectional samples for SEM analysis is also time-consuming, and thus costly. As such, routine SEM inspection is not a very effective measure of the metallization film quality.

Other techniques for measuring the quality of metallization films have been reported as under development. Magnetic force microscopy measures variations in magnetic flux caused by voids in the metallization; of course, this measurement not only requires current to be conducted through the conductor during measurement, but also highly precise magnetic field detection elements. Surface acoustic wave (SAW) microscopy has also been proposed, in which variations in reflection of acoustic waves due to voids may be measured, but resolution considerations tend to limit the applicability of SAW microscopy to small geometries.

BRIEF SUMMARY OF THE INVENTION

It is therefore an object of the present invention to provide a non-destructive method of inspecting the quality of small-geometry metallization in integrated circuits.

It is a further object of the present invention to provide such a method in which the inspection technique directly relates to, the film construction, such as by way of differential absorption of incident electromagnetic radiation.

It is a further object of the present invention to provide such a method in which large portions of the integrated circuit maybe efficiently inspected, so as to be performable in-line.

It is a further object of the present invention to provide such a method in which metallization voids may be distinguished from particles in the film.

It is a further object of the present invention to provide such a method in which the results from the inspection may readily be correlated to visually apparent film defects, such as scratches and larger particles.

It is a further object of the present invention to provide such a method in which the wafer inspection maybe carried out in a non-contact manner.

Other objects and advantages of the present invention will be apparent to those of ordinary skill in the art having reference to the following specification together with its drawings.

The present invention may be implemented into an apparatus and method for inspecting integrated circuit wafers at various stages of manufacture, particularly after the formation of one or more layers of metallization (typically copper or aluminum), patterned into metal conductors. Inspection is carried out by exposing the wafer to locally focused x-ray energy, through submicron apertures in an exposure array that is otherwise opaque to x-rays. A detector array is disposed on the opposite side of the wafer, having apertures therein that are physically registered to the apertures of the exposure array. The detector array spatially indicates the locations at which transmitted x-ray energy passes through the wafer; these indications can be used to identify the location of voids or other defects in the overlying metallization. Repeated exposures in combination with indexing of the wafer relative to the exposure and receiving apertures, effectively scans the wafer. Image processing or other signal analysis can be applied, resulting in a viewable image of the wafer or alternatively in the automated detection and differentiation of voids and other defects.

DETAILED DESCRIPTION OF THE INVENTION

As will be apparent to those skilled in the art having reference to this specification, it is contemplated that the present invention may be used with benefit in the inspection and analysis of semiconductor wafers of varying construction and layout. For clarity of description, this specification will use the example of a silicon single-crystal wafer upon which multiple levels of copper metallization are formed by way of a damascene process. It is to be understood, however, that the present invention may be used in connection with other metallization, such as aluminum metallization, and in connection with integrated circuit wafers formed of other semiconductor materials and combinations thereof.

Figure 1:
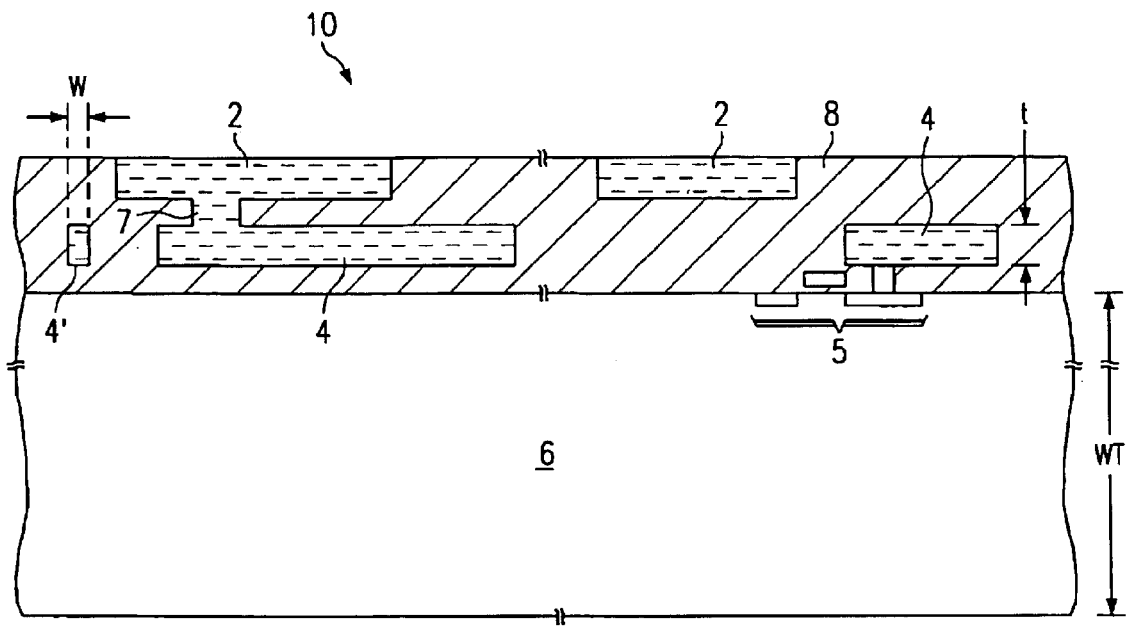
FIG. 1 is a cross-sectional view of a portion of an exemplary semiconductor wafer having a copper metallization layer at a surface thereof, to which the preferred embodiment of the present invention may be applied.

Referring first to FIG. 1, the principle of operation of the preferred embodiment of the present invention will now be described relative to integrated circuit wafer 10. As shown in FIG. 1, wafer 10 includes copper conductors 2, 4, arranged in multiple levels, near its top surface, and insulated from one another and from underlying semiconductor substrate 6 (formed, for example, as single-crystal silicon) by way of dielectric material 8. In this example, copper conductors 2 in an upper level are disposed above copper conductors 4 in a lower level, with copper plug 7 interconnecting conductors 2, 4 in the levels at selected locations. Additionally, the copper metallization may make contact to underlying active and passive circuitry structures, such as shown in FIG. 1 where one of lower level copper conductors 4 is in contact with the source/drain region of transistor 5.

One common technology for the fabrication of multiple levels of copper conductors 2, 4 is referred to in the art as the "damascene" process, in which the copper conductors 2, 4 are effectively inlaid into slots or tracks etched into an insulator layer (or multilayer dielectric film). According to this process, a relatively thin layer of copper is initially deposited over the etched dielectric material (and possibly over an adhesion layer of a refractory metal compound), to serve as a seed layer. The remainder of the copper metatization layer, which will generally be the large majority of the thickness of the copper film, is then electroplated overall. Chemical-mechanical polishing (CMP) of the wafer levels off the electroplated copper layer to the top surface of the insulator layer, inlaying copper conductors 2, 4 at the desired locations. Additional insulating layers and copper conductive levels are then formed as desired, for example by way of additional iterations of the damascene process. Vias through the dielectric may be filled with copper, tungsten, or some other metal, to interconnect conductors 2, 4 residing in differing metallization levels, for example as shown by plug 7 of FIG. 1.

Of course, following the fabrication of all levels of metallization specified by the design of the overall integrated circuit, wafer fabrication will generally be completed by the application of a protective overcoat, through which openings to metal bond pads or other connective lands are made. Following wafer fabrication and any desired electrical testing of the integrated circuits in wafer form, such "back-end" processes as dicing of the individual circuits from the wafer, electrical test, packaging, burn-in, and additional electrical testing, are then typically performed to result in a packaged integrated circuit that may then be implemented into end equipment; it is understood that such additional wafer fabrication and back-end processes shall not constitute a material change in the integrated circuit structure described herein.

The arrangement illustrated in FIG. 1 is not to scale, particularly in its illustration of the relative thicknesses of copper conductors 2, 4 relative to the thickness of silicon substrate 6. According to modern integrated circuit fabrication technologies, the thickness t of copper conductors 2, 4 may range from on the order of 0.5 $\mu$m (e.g., formed into a 0.5 $\mu$m trench in dielectric 8) to 1.0 $\mu$m at via 7. Also according to modern technologies, the minimum width w of metal conductors 2, 4 may be less than 1.0 $\mu$m, for example as shown by conductor 4' of FIG. 1. For example, it is contemplated that minimum width w of conductors 2, 4 may be as narrow as 0.25 $\mu$m using state-of-the-art technologies. On the contrary, wafer thickness wt may be on the order of 600 to 725 $\mu$m for wafers of conventional diameter such as 200 mm and larger.

The present invention is intend ed to be able to detect the presence of relatively small (e.g., on the order of 0.2 $\mu$m diameter) voids in copper conductors 2, 4. According to the preferred embodiment of the invention, this detection is carried out by the irradiation of wafer 10 with x-ray energy. X-ray energy is then detected on the opposite side of wafer 10, for example by way of an array of solid-state detectors, as will be described hereinbelow), to measure the transmission therethrough. The spatial arrangement of the transmitted energy is analyzed, providing an image of the structure of wafer 10. In principle, the present invention depends upon the differential absorption of x-ray energy between copper conductors 2, 4 that are whole versus those that have voids therein, rendering the voids visible in the analysis of the detect ed x-rays. In theory, such distinction can be readily made. In practice, however, because of the relatively large thickness (and corresponding x-ray absorption) of silicon substrate 6, and also because of the geometry of wafer 10 itself, the ability to differentiate between whole and voided copper conductors 2, 4 necessitates certain considerations in carrying out the x-ray analysis, as will now be described.

According to well-known x-ray theory, one may express an x-ray intensity I that is transmitted through a medium of thickness x as a function of an incident x-ray intensity $I_0$ and the x-ray absorption coefficient) of the medium, as follows:

$$I = I_0 exp(-\mu x)$$

In order to distinguish the absence (or, conversely, presence) of a portion of the material of a thickness $\Delta x$, one may consider a differential x-ray intensity $\Delta I$:

$$|\Delta I| = I_0 \mu \exp(-\mu x) \Delta x$$

As such, the differential x-ray intensity $\Delta I$ increases with increasing absorption coefficient $\mu$, because a higher absorption of energy by a material will necessarily result in increased contrast between locations having and not having the material. Void detection, for example, is enhanced by a high x-ray absorption coefficient $\mu$. The absorption coefficient $\mu$ depends not only upon the density of the material, but also upon the x-ray energy itself. In particular, the absorption $\mu$ of x-ray energy, at a given wavelength and for a given electron shell of the material, varies with the $(5/2)^{nd}$ power of the ratio between the binding energy and the photon energy. Additionally, the absorption $\mu$ also depends upon the wavelength of the x-ray energy.

It has also been observed, in connection with the present invention, that a relatively thick silicon substrate 6, upon which copper conductors 2, 4 are disposed, dictates certain tradeoffs in the selection of x-ray energy, according to the preferred embodiment of the present invention. Because a high x-ray absorption coefficient $\mu_{Cu}$ facilitates the detection of voids in copper conductors 2, 4, one would be led to select x-ray wavelength and energy ratios that maximize absorption coefficient $\mu_{Cu}$. However, the same factors of wavelength and energy ratio that maximizes the absorption coefficient $\mu_{Cu}$ in copper will also maximize the x-ray absorption coefficient $\mu_{Si}$ of silicon. Referring to FIG. 1, if the x-ray absorption of thick silicon substrate 6 is too high, substantially no x-rays can be transmitted through wafer 10 and therefore the differential absorption due to voids in copper conductors 2, 4 cannot be detected.

Figure 2:
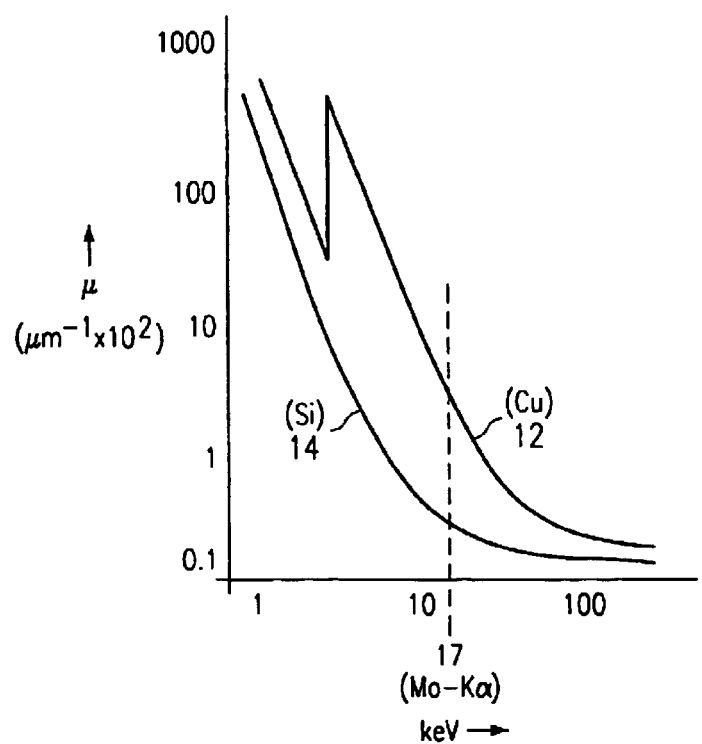
FIG. 2 is a plot of absorption coefficient versus x-ray energy for copper and silicon.

It is therefore useful, according to the preferred embodiment of the invention, to consider the differential absorption between the substrate material (e.g., silicon) and the metallization (e.g., copper) in selecting the x-ray parameters to be used. Referring now to FIG. 2, this differentiation will now be described.

FIG. 2 includes plots 12, 14 of x-ray absorption as a function of energy (or wavelength), for copper and silicon, respectively. As indicated in FIG. 2, plot 14 of the absorption coefficient $\mu_{Si}$ of silicon lies below plot 12 of the absorption coefficient $\mu_{Cu}$ of copper, at all energies. This relationship is, of course, due to the difference in atomic density and weight of the materials. As evident from FIG. 2, significant differentiation in these absorption coefficients is present at x-ray energies from about 5 keV up to about 100 keV.

One conventional x-ray production technique utilizes the bombardment of a molybdenum rotating anode to produce K$\alpha$-band x-rays at 17 keV (among other wavelengths). As shown in FIG. 2 by plots 12, 14, relatively good differentiation between absorption coefficient $\mu_{Cu}$ and absorption coefficient $\mu_{Si}$ is present at this energy. Specifically, for these Mo K$\alpha$ x-rays, absorption coefficient $\mu_{Cu}$ is approximately 0.0442/$\mu$m, and absorption coefficient $\mu_{Si}$ is approximately 0.0015/$\mu$m.

For the case of wafer 10 illustrated in FIG. 1, the relative difference signal between locations of one of copper conductors 2, 4 and away therefrom has been determined. For 600 $\mu$m of silicon, one may readily determine that the transmitted x-ray intensity I is approximately 0.40 of incident x-ray intensity $I_0$. By similar calculations, a copper conductor of 1.0 $\mu$m will absorb approximately 4% of the incident x-ray intensity (specifically, transmitting 0.956762 of the incident energy). The theoretical effect of a 0.2 $\mu$m void in a copper conductor 2, 4 that is otherwise 1.0 $\mu$m thick may be modeled by the transmission ratio $I/I_0$ of a 0.8 $\mu$m copper conductor which, in this case, is calculated to be 0.965257. As a result, assuming approximately 40,000 photons as the incident energy and requiring x-ray transmission through the entire thickness of wafer 10, a difference signal of about 400 photons would be presented by a 0.2 $\mu$m void within a 1.0 $\mu$m thick copper conductor 2, 4. Even with Gaussian noise of on the order of 200 photons, the signal-to-noise ratio of 2 is contemplated to be sufficient to detect the presence of a void. Conventional image processing techniques, such as Fast Fourier Transform (FFT) analysis in the form of periodograms, could also be applied to enhance this signal.

It is contemplated that other defects, such as particles or filaments, may also be detected according to the present invention. Such defects may absorb more (rather than less) x-ray energy than expected for a given location of wafer 10, and in this manner also become detectable through operation of the present invention.

With reference to FIG. 2, it is apparent from a comparison of plots 12, 14 that lower energy x-rays may provide better visibility of the features of copper metallization than the 17 keV x-rays, considering that a greater difference in the absorption coefficients $\mu_{Cu}$, $\mu_{Si}$ is present at these lower energies. This wider separation permits variations in the copper absorption (such as occurs due to voids) to be more visible, perhaps with fewer photons, because of the reduced relative absorption in the silicon substrate. However, these lower energies, such as 8 keV, are not readily derivable from rotating-anode x-ray generators, and require the use of laser harmonics, synchotron undulators, and other complex wavelength-tunable x-ray equipment. If such generation equipment is economically available in a manufacturing facility, however, it is contemplated that improved detection capabilities would be provided according to the preferred embodiment of the invention.

Additionally, it is contemplated that the use of complex x-ray generation equipment for which the energy wavelength may be tuned can enable additional defect analysis. For example, it is contemplated that certain non-void defects, such as slurry residue and particle defects, may be sensitive to x-ray wavelengths other than that absorbed by the metal of conductors 2, 4. As such, laser harmonics, synchotron undulators, and other complex wavelength-tunable x-ray equipment may be used to image wafer 10 at multiple wavelengths. Comparison of the results of x-rays at multiple energies may provide further characterization of defects that may be detected. The simultaneous analysis of multiple wavelengths may also be performed by energy dispersive analysis, and is possible with most solid state x-ray detectors.

It has been observed, in connection with the present invention, that the presence of a 1.0 $\mu$m copper conductor at a surface of a 600 $\mu$m thick silicon wafer can be detected by the application of x-ray energy. In particular, imaging of the presence of such a copper conductor has been made using 17 keV Mo K$\alpha$ x-rays, imaged onto a photographic emulsion-based Lang x-ray shadowgraph, despite the relatively poor dynamic range of the emulsion.

In addition to the selection of the x-ray energy and wavelength to be used, another consideration in carrying out the x-ray analysis according to the preferred embodiment of the invention addresses difficulties that are presented by the geometry of the semiconductor wafer. In particular, the spatial resolution provided by conventional x-ray exposure is not suitable for imaging of a wafer, particularly in attempting to analyze extremely small features such as sub-micron conductors. This inadequate spatial resolution was evident in the shadowgraph image mentioned above.

Figure 3:
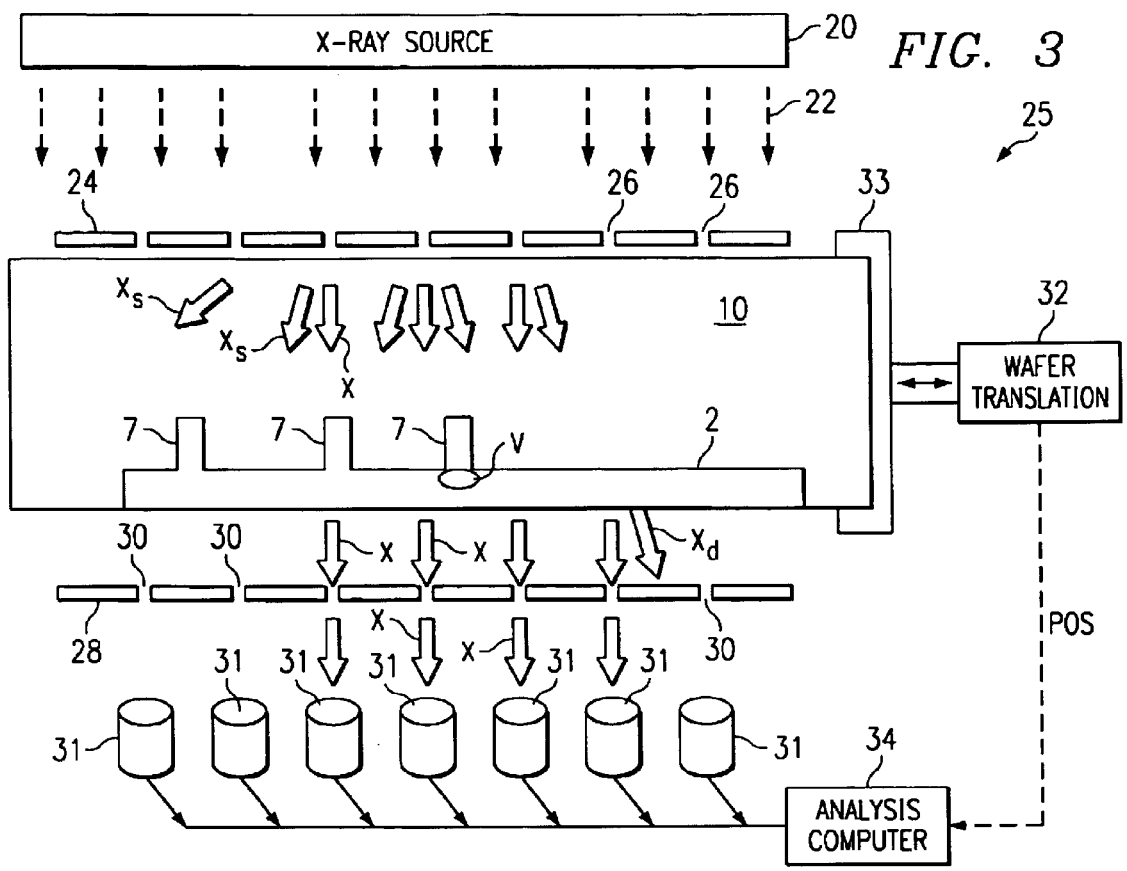
FIG. 3 is a cross-sectional schematic view of a system for performing x-ray inspection of integrated circuit wafers according to the preferred embodiment of the invention.

Referring now to FIG. 3, the construction of x-ray imaging system 25 for use in providing x-ray analysis of small, sub-micron, metallic conductor lines at the surface of a semiconductor integrated circuit wafer, according to the preferred embodiment of the invention, will now be described. According to this preferred embodiment of the invention, imaging of small features at a wafer surface may be carried out with sufficient signal strength and resolution as to detect the presence and location of voids.

In the schematic illustration of FIG. 3, system 25 includes x-ray source 20 for generating collimated x-ray energy 22. As discussed above, x-ray source 20 may be of the rotating anode type, such as used to generate Mo Kα band x-ray energy at 17 keV; alternatively, x-ray source 20 may be realized by way of laser harmonics, synchotron undulators, and the like, for generating x-ray energy of an optimized energy, particularly to select a wavelength at which the absorption coefficients of the metal conductor material and the semiconductor material substantially differ. Collimation of x-ray energy 22 by source 20 is preferably accomplished in the conventional manner according to well known techniques, so that x-ray energy 22 generated by x-ray source 20 is substantially unidirectionally aimed at a surface of wafer 10, as shown in FIG. 3.

According to the preferred embodiment of the invention, collimated x-ray energy 22 is directed at aperture array 24, which is disposed in proximity to wafer 10 as shown in FIG. 3 to improve the resolution of the x-ray imaging performed by system 25. In this regard, aperture array 24 is formed of a high atomic number metal (e.g., gold, or lanthanum), with small openings 26 formed therethrough that are preferably arranged in a two-dimensional array (only one dimension of which is visible in FIG. 3). The size of openings 26 is determined primarily by the minimum size of voids or defects in conductors 2, 4 that are to be detectable by system 25. Preferably, the size of openings 26 will be on the order of ½ of the minimum detectable defect size. For example, for conductors 2, 4 of a width of on the order of 0.25 μm, important defects may be as small as 0.15 μm in size, requiring the size of openings 26 in aperture array to be on the order of 0.075 μm. As such, aperture array 24 is itself preferably formed by way of photolithography or direct e-beam writing. In this regard, it is contemplated that aperture array 24 may be constructed of an x-ray transparent substrate material, upon which a layer of the high atomic number metal is deposited and photolithographically patterned so as to form openings 26 in the metal film.

The arrangement of openings 26 in aperture array 24, a nd the proximity of aperture array 24 to wafer 10, are selected in such a manner as to maximize the irradiation of wafer 10 with x-ray energy that is as perpendicularly oriented as possible, in order to maximize the resolution of the resulting image. In order to maximize this directionality, aperture array 24 is preferably placed as closely as possible to wafer 10. Indeed, considering th at wafer 10 is irradiated from back to front (as will be further described hereinbelow), aperture array 24 may actually be paced in contact with wafer 10, although non-contact placement is preferred. In this regard, the spacing of openings 26 may depend upon such factors as the crystal orientation of the semiconductor material of wafer 10, the pitch of conductors 2, 4 thereupon, the precision with which wafer 10 is indexed with in system 25 (as will be described hereinbelow), and the like. For wafers 10 fabricated according to modem fabrication technology, the separation between adjacent openings 26 in aperture array 24 maybe on the order of 1 mm, for example.

As noted above, wafer 10 is preferably disposed in an upside-down manner, according to the preferred embodiment of the invent ion, as shown in FIG. 3. This orientation imparts x-ray energy 22 into the backside of wafer 10, which is the surface of wafer 10 opposite from the frontside at which conductor 2 is disposed in this example. This orientation of wafer 10 is preferred, according to the present invention, because it permits the x-ray energy to leave wafer 10 immediately after transmission through conductor 2. As shown in FIG. 3, significant scattering and diffraction of x-ray energy occurs within wafer 10, due primarily to the crystalline structure of substrate 6. FIG. 3 qualitatively illustrates this scattering by rays Xs which, as compared with x-ray rays X in FIG. 3, are directed at an angle from the normal. The resolution of the eventual image produced by conductor 2, in response to its absorption of x-ray energy, is of course optimized by the bulk of the x-ray energy impinging upon, and transmitting through, conductor 2 in a normal direction thereto; conversely, scattered x-ray energy such as illustrated by rays Xs will disrupt the resolution at which conductors 2 may be imparted. As a result, the pattern of x-ray transmission from the frontside of wafer 10 will more closely match the location of metal material in the pattern of conductors 2 (and voids V therein), than if these same transmitted x-rays were subject to additional scattering by substrate 6 of wafer 10. As such, the eventual signal-to-noise ratio of the imaging carried out by system 25 according to this preferred embodiment of the invention is improved by this orientation.

The necessity of this upside-down orientation of wafer 10 is somewhat reduced if wafer 10 is backside-polished, considering the decrease in scattering provided by such polishing.

The particular location of wafer 10 that is irradiated and imaged by system 25 may vary, depending upon the application. As is known in the art, test structures are often helpful in the characterization and monitoring of a manufacturing process. Such test structures are typically formed on specific test wafers, and also as test die within a production wafer that also includes "live" integrated circuit die. Test structures having repetitive metal conductor structures are contemplated to be especially useful in connection with the present invention, due to the ease with which openings 26 of aperture array 26 may be registered with such regular structures; additionally, the correlation between imaging of the test structures with electrical measurements such as continuity and resistance of such structures may readily be made. Alternatively, of course, actual functional integrated circuit structures may also be imaged according to this preferred embodiment of the invention.

Aperture array 28 is disposed near the frontside of wafer 10, having openings 30 therethrough in a pattern that matches the pattern of openings 26 in aperture array 24. Aperture array 28 is constructed of a high atomic number metal, similarly as described above relative to aperture array 24, with openings 26 formed by way of photolithography. The high atomic number metal of aperture array 28 substantially absorbs x-ray energy imparted thereto. According to this preferred embodiment of the invention, aperture array 28 is registered with aperture array 24 so that respective ones of openings 26, 29 line up with one another; in this way, any normally-directed x-ray energy 22 that passes through openings 26 in aperture array 24 and wafer 10 will thus be able to pass through corresponding openings 30 in aperture array 28 (as shown by rays X in FIG. 3). X-ray energy that is diffracted or scattered by wafer 10, such as shown in FIG. 3 by ray $X_d$ for energy diffracted by conductors 2, is thus absorbed by aperture array 28.

X-ray detectors 31 are arranged in an array below aperture array 28 in system 25 according to the preferred embodiment of the invention. As illustrated in FIG. 3, each of x-ray detectors 31 is associated with a corresponding one of openings 30 in aperture array 28. Because of the beam-shaping effect of aperture arrays 24, 28, the x-ray energy received by each detector 31 is substantially limited to x-ray energy that is transmitted in a normal direction through wafer 10 at the location of wafer 10 defined by its corresponding openings 26, 30, localizing the x-ray transmission detected by system 25. X-ray detectors 31 are preferably realized by conventional solid-state x-ray detectors, such as those constructed of lithium-drifted silicon, or of gallium arsenide or other III-V semiconductor devices that are x-ray sensitive.

Each detector 31 is coupled to analysis computer 34, to which signals corresponding to the detected x-ray energy are communicated. Analysis computer 34 may be constructed as a conventional microprocessor-based computer, having processing and data storage capability sufficient to store digital signals corresponding to the x-ray energy detected by each of detectors 31, as obtained from one or more wafers 10, as well as the locations of each wafer 10 to which the detected x-ray energy correspond. In this regard, system 25 further includes wafer translation system 32, which holds wafer 10 by way of clamp 33, and which laterally translates wafer 10 in system 25 relative to aperture arrays 24, 28 and detectors 31. Wafer translation system 32 permits x-ray imaging of various selected locations of the same wafer 10 using system 25, without requiring either a full-wafer imaging system or openings 26, 30 to be spaced at the actual desired resolution. The position of wafer 10 relative to aperture arrays 24, 28 may be communicated to analysis computer 34 by wafer translation system 32, over signal line POS as shown in FIG. 3. Knowledge of the position of wafer 10 at the time of the receipt of x-ray transmission signals from detectors 31 enables analysis computer 34 to map the x-ray transmission through wafer 10 into an overall image, for use in analysis. Additionally, analysis computer 34 also performs energy dispersive spectroscopy analysis, so as to exclude the effects of any fluorescent x-ray generation caused by the x-ray irradiated silicon substrate 6, and to allow for multiple x-ray wavelengths, if utilized.

Figure 4:
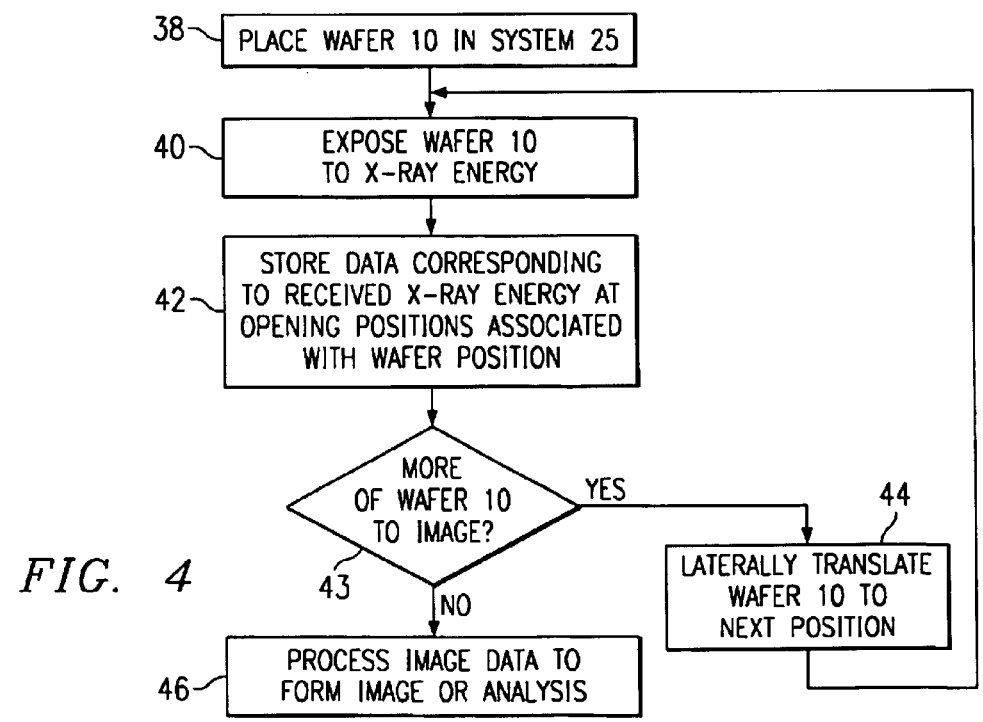
FIG. 4 is a flow diagram illustrating the operation of the system of FIG. 3 according to the preferred embodiment of the invention.

The operation of system 25 in imaging wafer 10 according to the preferred embodiment of the invention will now be described relative to the flow chart of FIG. 4, and of course with reference to the schematic diagram of FIG. 3. The operation of system 25 begins, of course, with the placement of wafer 10 into system 25, between aperture arrays 24, 28 as shown in FIG. 3. As described above, particularly if wafer 10 is not double-side polished, it is preferable to orient wafer 10 so that the active surface (i.e., having conductors 2, 4 and plus 7 thereat) is away from x-ray source 20, so that x-ray energy leaves from, rather than enters, the frontside of wafer 10. Wafer translation system 32 preferably finely places wafer 10 within system 25, registered to a desired initial scan location therein, and communicates this position to analysis computer 34 by way of signals on lines POS.

In process 40, x-ray source 20 generates collimated x-ray energy 22, and irradiates wafer 10 through aperture array 24. It is contemplated that process 40 corresponds to a burst of x-ray energy, having a photon count determined according to the signal-to-noise ratio expected from this operation of system 25, as well as the absorption of energy by wafer 10. As noted above, a photon count of on the order of tens of thousands of photons (per opening 26) is contemplated to provide a suitable image for typical applications.

As described above relative to FIG. 3, the irradiated collimated x-ray energy 22 impacts wafer 10 in substantially a normal direction relative to its surface, at locations corresponding to openings 26 in aperture array 24. Also as noted above, openings 26 are preferably arranged in a two-dimensional array, to improve throughput of the imaging process. X-ray energy 22 applied to wafer 10 through openings 26 in process 40 thus passes through wafer 10, to the extent not absorbed by the material thereof. To the extent that the energy is not diffracted, scattered, or absorbed within wafer 10, x-ray energy 22 that passes through an opening 26 then passes through a corresponding opening 30 in aperture array 28 on the opposite side of wafer 10, and is received at a corresponding x-ray detector 31. Detectors 31 generate electrical signals corresponding to the magnitude of the x-ray energy detected thereat, and communicate these signals to analysis computer 34. In process 42, analysis computer 42 stores digital data corresponding to the signals received from detectors 28 in this instance, such data being stored in association with the current location of wafer 10 receiving the x-ray radiation, as indicated by wafer translation system 32 over lines POS.

Decision 43 is then performed by system 25 to determine whether additional locations of wafer 10 are to be imaged by x-ray system 25. If so (decision 43 is YES), wafer translation system 32 laterally translates wafer 10 to the next position for imaging, in process 44, following which imaging processes 40, 42 and decision 43 are again carried out. The translation of process 44 will typically be carried out in a two-dimensional manner, for example in a manner similar to a raster scan, in order to provide coverage over wafer 10. The extent of the movement of process 44 depends upon the type of scanning that is being carried out in this process, the memory capacity of analysis computer 34, and other such factors.

For example, relative to FIG. 3, inspection of wafer 10 to detect voids such as void V in metal conductors 2 and plugs 7 may require relatively slight incremental lateral translation in process 42. In the state illustrated in FIG. 3, while void V is certainly of a detectable size, its current position is not in-line with openings 26, 30 of aperture arrays 24, 28, respectively, and as such void V would not be detected by the instance of processes 40, 42 at this point in time. In order to rigorously inspect the portion of wafer 10 shown in FIG. 3 so as to be able to detect void V, the translation of process 44 is preferably a very slight incremental indexing, for example of on the order of one micron or less. Such indexing would provide thorough coverage of at least a portion of wafer 10.

Alternatively, if the imaging to be carried out by system 25 is intended to generate a statistical sample over a wide area of wafer 10, the translation of process 44 may be quite substantial. For example, the same location of each of the integrated circuit die being fabricated on wafer 10 may be inspected with each instance of processes 40, 42, to provide a sample size of the number of openings 26 times the number of die on wafer 10. In such operation, translation process 44 would simply step from die to die on wafer 10, so that each die is separately imaged. It is contemplated that this, and other, alternative approaches to the gathering of image data using system 25 will be apparent to those skilled in the art having reference to this specification.

Upon completion of the imaging of wafer 10 (decision 43 is NO), system 25 next performs process 46, by way of analysis computer 34 executing a program to perform the desired analysis or imaging of the received and stored data. Many alternative analysis approaches for process 46 are contemplated according to the present invention, some of which will now be described.

According to a first example, analysis process 46 may generate an x-ray image of one or more die on wafer 10. In such an imaging approach, the stored digital data corresponding to the received x-ray energy is simply arranged according to wafer location, and displayed on a graphics display or by way of a printer by way of an image in which the intensity of each pixel corresponds to the intensity of the x-ray energy received at that corresponding wafer location. In this regard, conventional image processing techniques, such as FFT-based image processing, may be applied in order to improve image quality for viewing. A human analyst may then inspect the displayed or printed image to find any defects, such as voids, present therein, or to correlate the imaged location of the wafers with known circuit failures found by electrical testing of the integrated circuits.

Another exemplary approach to analysis process 46 may include an automated analysis of the image data. According to this approach, the x-ray image data corresponding to identical locations of multiple die on wafer 10 may be statistically combined, with each location of each then being compared against the distribution of data for that location over all die on wafer 10. Outliers (i.e., die locations having data that differs from the distribution in a significantly significant way) can then be identified, as such outliers may well correspond to defects such as voids, particles, filaments, or the like. Additionally, image processing including positive/negative contrast techniques may be applied in process 46, in order to distinguish voids and scratches (i.e., absence of conductor material) from particle defects such as slurry residue or inclusions (i.e., presence of undesired material). In the case of voids and scratches, analysis computer 34 may also carry out some type of spatial processing, linking identified defects on wafer 10, in order to distinguish a localized void from a scratch over several die. In any case, this automated analysis may also be applied among multiple wafers 10, for example in the development of a historical trend or distribution against which newly examined wafers 10 are compared. In this regard, it is contemplated that this type of analysis may be best applied by examining test die on wafers 10, rather than live integrated circuit die. The analysis of test die also eliminates any concern regarding potential degradation of circuit functionality due to photoelectrons that may be generated by x-ray exposure of silicon and trapped at transistor gates (if left unannealed).

It is contemplated that the selection and use of these, and other, implementations of process 46 may be readily selected by those skilled in the art having reference to this specification, based upon the particular monitoring and analysis needs of specific manufacturing processes.

The present invention provides many benefits in the manufacture of integrated circuits, primarily in providing a non-destructive and non-invasive inspection tool for extremely small features in the integrated circuit. The resolution with which examination of the integrated circuit wafers may be inspected is contemplated to be extremely fine, thus permitting non-destructive inspection to detect extremely small, yet killing, defects in these conductors. Furthermore, such detection may be carried out for integrated circuits having multiple levels of metal conductors. The ability to obtain inspection results in this manner further enables the inspection of wafers while in the manufacturing process, prior to obtaining electrical functionality test results on the same wafers. As a result, the volume and quality of inspection data that may be obtained in this manner can be greatly increased through implementation of the present invention, providing a large amount of reliable data that can be used to improve manufacturing yields.

While the present invention has been described according to its preferred embodiments, it is of course contemplated that modifications of, and alternatives to, these embodiments, such modifications and alternatives obtaining the advantages and benefits of this invention, will be apparent to those of ordinary skill in the art having reference to this specification and its drawings. It is contemplated that such modifications and alternatives are within the scope of this invention as subsequently claimed herein.

We claim:

1. A system for imaging a semiconductor wafer to detect defects therein, comprising:
   an x-ray source for generating collimated x-rays;
   a first aperture array, having a plurality of openings therethrough through which the collimated x-rays are substantially transmitted;
   a second aperture array, having a plurality of openings therethrough through which x-rays may be substantially transmitted, the openings of the second aperture array being aligned with openings of the first aperture array, the first and second aperture arrays spaced apart from one another with an area for a semiconductor wafer therebetween, the first aperture array being nearer the x-ray source than the second aperture array;
   a detector array for detecting x-ray energy transmitted through the openings of the second aperture array; and
   an analysis computer, coupled to the detector array, to receive signals therefrom corresponding to the detected x-ray energy.

2. The system of claim 1, wherein the first and second aperture arrays each comprise a film of high atomic number metal, through which the openings are disposed.

3. The system of claim 1, wherein the x-ray source comprises:
   a rotating anode x-ray source.

4. The system of claim 1, wherein the x-ray source comprises a wavelength-tunable x-ray source.

5. The system of claim 1, further comprising:
   a wafer translation system, for controllably translating the semiconductor wafer when disposed between the first and second aperture arrays.

6. The system of claim 5, wherein the wafer translation system is coupled to the analysis computer;
   and wherein the analysis computer is for storing digital data corresponding to the detected x-ray energy in association with positional information communicated thereto by the wafer translation system.

7. The system of claim 1, wherein the detector array comprises:
   a plurality of solid-state x-ray detectors, each associated with one of the plurality of openings of the second aperture array, each for generating a signal corresponding to the magnitude of x-ray energy transmitted through its associated opening of the second aperture array, and for communicating the signal to the analysis computer.

8. A method of detecting defects in a semiconductor wafer, comprising the steps of:
   placing a semiconductor wafer between first and second aperture arrays, each of the first and second aperture arrays having a plurality of openings therethrough, through which x-ray energy may be transmitted, the openings of the second aperture array being aligned with openings in the first aperture array;

irradiating the first aperture array with x-ray radiation, so that x-ray radiation first passes through the plurality of openings through the first aperture array, then through the semiconductor wafer, and then through the plurality of openings through the second aperture array; and detecting x-ray radiation transmitted through the second aperture array.

9. The method of claim 8, further comprising:

generating an image from the detected x-ray radiation.

10. The method of claim 9, wherein the detecting step comprises:

detecting x-ray radiation with a plurality of detectors, each associated with one of the plurality of openings through the second aperture array.

11. The method of claim 9, wherein the generating step comprises:

communicating a signal from each of the plurality of detectors to an analysis computer, the signal corresponding to the magnitude of x-ray radiation detected by the detector; and operating the analysis computer to associate the communicated signals with a spatial location for the wafer.

12. The method of claim 11, wherein the irradiating and detecting steps are performed for a first location of the semiconductor wafer relative to the pluralities of openings through the first and second aperture arrays;

and further comprising:

after the detecting step, laterally translating the semiconductor wafer to a second location relative to the pluralities of openings through the first and second aperture arrays;

after the translating step, repeating the irradiating and detecting steps for the wafer at the second location.

13. The method of claim 11, further comprising:

operating the analysis computer to identify spatial locations of contrasting detected x-ray radiation, so that defects corresponding to the absence of conductor material may be distinguished from defects corresponding to the presence of undesired material.

14. The method of claim 11, further comprising:

operating the analysis computer to perform spatial processing of detected defects.

15. The method of claim 8, wherein the irradiating and detecting steps are performed for a first location of the semiconductor wafer relative to the pluralities of openings through the first and second aperture arrays;

and further comprising:

after the detecting step, laterally translating the semiconductor wafer to a second location relative to the pluralities of openings through the first and second aperture arrays;

after the translating step, repeating the irradiating and detecting steps for the wafer at the second location.

16. The method of claim 15, further comprising:

after each of the detecting steps, communicating a signal from each of the plurality of detectors to an analysis computer, the signal corresponding to the magnitude of xray radiation detected by the detector;

operating the analysis computer to store digital data corresponding to the communicated signal from each of the plurality of detectors, the digital data stored in association with the location of the semiconductor wafer relative to the pluralities of openings through the first and second aperture arrays.

17. The method of claim 16, further comprising:

generating an image of the semiconductor wafer from the stored digital data.

18. The method of claim 16, wherein the first and second locations correspond to identical locations of first and second integrated circuit die on a surface of the semiconductor wafer;

and further comprising:

comparing the digital data stored in association with the first and second locations of the semiconductor wafer.

19. The method of claim 16, further comprising:

repeating the placing, irradiating, detecting, communicating, and operating steps for a plurality of semiconductor wafers; and comparing the digital data stored in association with the locations of the plurality of semiconductor wafers.

* * * * *